United States Patent
Benjamin et al.

(10) Patent No.: US 7,759,386 B2
(45) Date of Patent: Jul. 20, 2010

(54) PHARMACEUTICAL COMPOSITIONS OF ESTROGENIC AGENTS

(75) Inventors: Eric Joel Benjamin, Pomona, NY (US); Wendy Ann Dulin, Sloatsburg, NY (US); Jiwaji Gulabrao Suryawanshi, Rockaway, NJ (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/943,269

(22) Filed: Nov. 20, 2007

(65) Prior Publication Data

US 2008/0269198 A1    Oct. 30, 2008

Related U.S. Application Data

(63) Continuation of application No. 09/896,226, filed on Jun. 29, 2001, now abandoned.

(60) Provisional application No. 60/216,192, filed on Jul. 6, 2000.

(51) Int. Cl.
*A61K 31/405* (2006.01)

(52) U.S. Cl. .................. 514/415; 514/315; 514/358; 514/416; 514/408

(58) Field of Classification Search .............. 514/415, 514/416, 408, 358, 315, 418, 317
See application file for complete search history.

(56) References Cited

U.S. PATENT DOCUMENTS

| | | | |
|---|---|---|---|
| 4,133,814 A | 1/1979 | Jones et al. | |
| 4,418,068 A | 11/1983 | Jones | |
| 5,332,727 A | 7/1994 | Birkmayer et al. | |
| 5,478,847 A | 12/1995 | Draper | |
| 5,480,652 A | 1/1996 | Bru-Magntez et al. | |
| 5,510,358 A | 4/1996 | Palkowitz | |
| 5,567,437 A | 10/1996 | Bru-Magniez et al. | |
| 5,747,510 A | 5/1998 | Draper | |
| 5,780,497 A | 7/1998 | Miller et al. | |
| 5,811,120 A | 9/1998 | Gibson et al. | |
| 5,880,137 A | 3/1999 | Miller et al. | |
| 5,919,800 A | 7/1999 | Palkowitz | |

FOREIGN PATENT DOCUMENTS

| | | |
|---|---|---|
| EP | 0 670 162 | 9/1995 |
| EP | 0 674 903 | 10/1995 |
| EP | 0 729 956 | 9/1996 |
| EP | 0 802 183 | 10/1997 |
| EP | 0 802 184 | 10/1997 |
| FR | 2698788 | 8/1976 |
| WO | WO-96/21656 | 7/1996 |
| WO | WO-99/19293 | 4/1999 |

OTHER PUBLICATIONS

International Search Report issued for PCT/US01/20993, dated Apr. 25, 2002.
Lachman, et al., The Theory and Practice of Industrial Pharmacy, pp. 689-690 (1970).
Lesson, et al., "Stability of Tetracycline and Riboflavin", J. of Pharmaceutical Sciences, 58(3):355-357 (1969).
Liebrman, et al., Pharmaceutical Dosage Forms—Tablets, 1:86-88 (1980).
Liebrman, et al., Pharmaceutical Dosage Forms—Tablets, 1:72-83 (1980).
Wells, Pharmaceutical Preformulation: The Physiochemical Properties of Drug Subastances, p. 171 (1988).
Sawicka, "The Influence of Excipients and Technological Process on Cholecalciferol Stability and Its Liberation from Tablets", Pharmazie, 46:519-521 (1991).
*Dictionary of Pharmaceutical Auxiliaries*, Schiuan Science and Technology Publishing House, pp. 19-22, 55-57, 72-73, 79, 82-85, 90-91, and 229 (1995)—Chinese Language.
Dictionary of Pharmaceutical Auxiliaries, Sichuan Science and Technology Publishing House, pp. 19-22, 55-57, 72-73, 79, 82-85, 90-91, and 229 (1995)—English Language Translation.
Niles, et al., "Chapter 3: Principles of Therapeutics", in *Goodman & Gilman's: The Pharmacological Basis of Therapeutics, Ninth Edition*, McGraw-Hill, pp. 43-62 (1996).
*Technologies of Applying Pharmaceutical Auxiliaries*, China Pharmaceutical Technology Publishing House, pp. 95-96 (1991)—Chinese Language.
Technologies of Applying Pharmaceutical Auxiliaries, China Pharmaceutical Technology Publishing House, pp. 95-96 (1991)—English Language Translation.

*Primary Examiner*—Sreeni Padmanabhan
*Assistant Examiner*—Shobha Kantamneni
(74) *Attorney, Agent, or Firm*—Ram W. Sabnis; Stephen E. Johnson

(57) ABSTRACT

This invention relates to novel pharmaceutical carrier or excipient systems and oral pharmaceutical compositions comprising 1-[4-(2-Azepan-1yl-ethoxy)-benzyl]-2-(4-hydroxyphenyl)-3-methyl-1H-indol-5-ol or 2-(4-Hydroxy-phenyl)-3-methyl-1-(4-(2-piperidin-1-yl-ethoxy)benzyl]-1H-indol-5-ol, or a pharmaceutically acceptable salt thereof.

3 Claims, No Drawings

PHARMACEUTICAL COMPOSITIONS OF ESTROGENIC AGENTS

CROSS REFERENCE TO RELATED APPLICATIONS

This application is a continuation of U.S. patent application Ser. No. 09/896,226, filed on Jun. 29, 2001, which claims the benefit of U.S. Provisional Application No. 60/216,192, filed Jul. 6, 2000.

FIELD OF THE INVENTION

This invention relates to pharmaceutical compositions utilizing compounds which have activity as estrogenic agents. This invention particularly relates to novel oral pharmaceutical compositions comprising one or more active pharmacological agents, such as TSE-424, ERA-923, raloxifene, tamoxifen, droloxifene, arzoxifene or CP 336156 and one or more pharmaceutically acceptable carriers or excipients.

BACKGROUND OF THE INVENTION

EP 0 802 183 A1 and U.S. Pat. No. 5,780,497 describe substituted indole compounds of the formulae below:

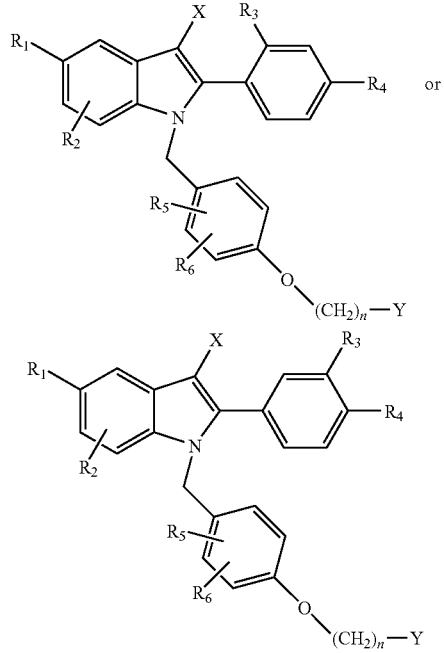

as well as their use as estrogenic agents, including the treatment of bone loss, cardiovascular disease, maladies associated with or resulting from the proliferation or abnormal development of endometrial or endometrial-like tissues, and disease states or syndromes associated with estrogen deficiency.

EP 0 802 184 A1, published Oct. 22, 1997, describes comparable uses for substituted indole compounds of the formulae below.

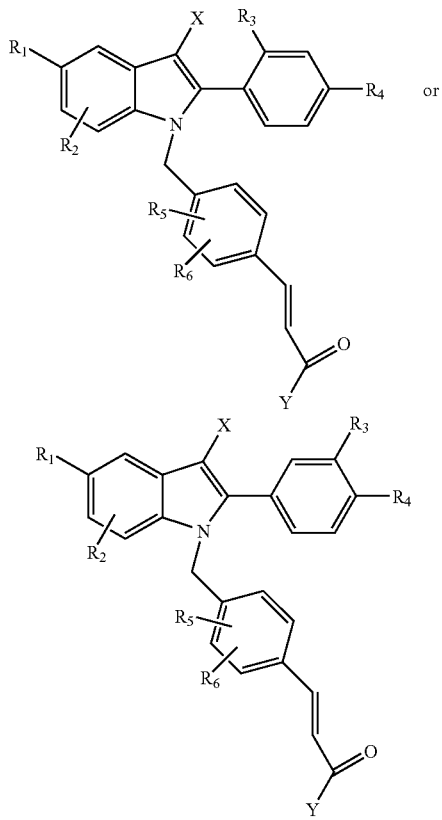

Analogous indole compounds having the general structures:

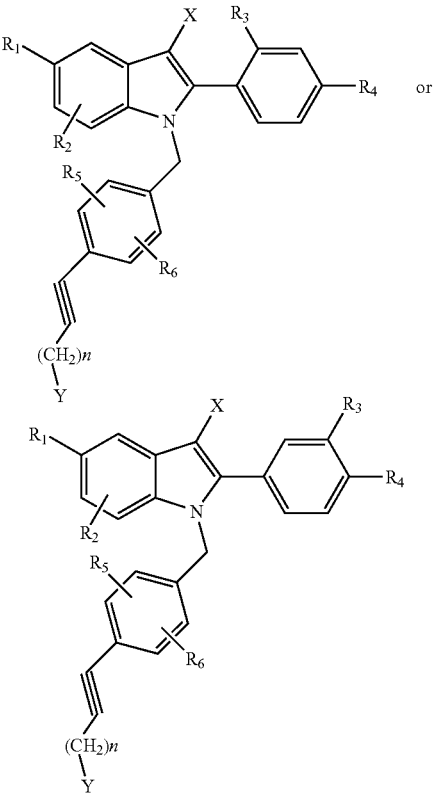

are described in U.S. Pat. No. 5,880,137 (Miller et al.).

U.S. Pat. No. 5,811,120 (Gibson, L. L. et al), titled "Solid orally administerable raloxifene hydrochloride pharmaceutical formulation" (Eli Lilly and Company), describes a composition and process for raloxifene hydrochloride tablets including a surfactant being a sorbitan fatty acid ester or a polyoxyethylene sorbitan fatty acid ester, polyvinylpyrrolidone (PVP), and a water soluble diluent which is a polyol or sugar. Raloxifene has low water solubility. The Gibson et al. patented composition claims the inclusion of PVP and a watersoluble diluent to achieve adequate solubility of raloxifene.

U.S. Pat. No. 5,747,510 (Draper) teaches pharmaceutical formulations containing raloxifene in a dose range of from about 55 to about 150 mg. U.S. Pat. No. 5,747,510 (Gibson et al.) provides raloxifene formulations utilizing a surfactant, polyvinylpyrrolidone and a water soluble diluent, particularly those in which the surfactant is a sorbitan fatty acid ester or a polyoxyethylene sorbitan fatty acid ester.

U.S. Pat. Nos. 5,510,358 (Palkowitz) and 5,919,800 (Palkowitz) teach the synthesis and use of Arzoxifene, its analogs and salt forms, with or without combination with estrogen, for the treatment of osteoporosis, post-menopausal syndrome, cardiovascular-related pathological conditions and estrogen-dependent cancer.

U.S. Pat. Nos. 5,332,727 and 5,480,652 describe the use of antioxidants such as ascorbic acid in a solid pharmaceutical composition to stabilize the drug. In the case of NADH and NADPH formulations, the stabilizers added to the formulation include $NaHCO_3$ and PVP in addition to ascorbic acid and are not added to the formulation for an antioxidant effect per se. In the case of ibuprofen, the antioxidant must be in intimate contact with the active drug agent prior to its incorporation into the formulation in order to achieve its protective effect. This effect is only needed in the presence of alkaline carbonates in these effervescent formulations.

WO 96/21656 (Cameron et al.) teaches novel compounds, including CP 336156, and uses for treating or preventing obesity, breast cancer, osteoporosis, endometriosis, cardiovascular disease and prostatic disease.

Sawicka, J. "The influence of excipients and technological process on cholecalciferol stability and its liberation from tablets", *Pharmazie,* 46 (1991), H. 7, pp. 519-521 describes the stabilization of cholecalciferol with various antioxidants in the solid state. The best antioxidant system described, however, yielded only 87.6% of the original content after 1 year of storage and the dissolution of the active material was also quite slow. Thus, improvements are required for stabilization of unstable solid drugs.

In light of the prior art, there is still a need to improve the solubility, stability and absorption qualities of poorly soluble pharmaceutical agents.

DESCRIPTION OF THE INVENTION

The present invention provides for orally administrable preparations that optimize the stability and enhance the dissolution of poorly soluble pharmaceutical agents, including estrogenic agents. Various formulations have been used to produce rapid dissolution of poorly soluble drugs, such as solubilization form (e.g. softgel capsules) or a high-energy form (e.g. solid dispersions). These techniques use specialized equipment and/or processes. The present invention provides pharmaceutically useful compositions which produce a rapid dissolution of poorly soluble drugs from a pharmaceutical solid dosage formulation via commonly used components and processes.

This invention comprises novel pharmaceutical carrier or excipient systems useful in the formulation of solid oral dosage forms for poorly soluble pharmacological agents, including estrogenic pharmacological agents including, but not limited to, those in the art known as TSE-424, ERA-923, raloxifene, tamoxifen, droloxifene, and arzoxifene, as well as their analogs and pharmaceutically acceptable salts. These carrier or excipient systems comprise:

a) a filler and disintegrant component comprising from about 5% to about 82% by weight (wght) of the total formulation, preferably between about 30% and about 80% of the formulation, of which from about 4% to about 40% by weight of the total formulation comprises one or more pharmaceutically acceptable disintegrants; and b) a lubricant comprising from about 0.2% to about 10% of the composition (wght), such as selected from the group of magnesium stearate or other metallic stearates (e.g. calcium stearate or zinc stearate), fatty acid esters (e.g. sodium stearyl fumarate), fatty acids (e.g. stearic acid), fatty alcohols, glyceryl behenate, mineral oil, parrafins, hydrogenated vegetable oils, leucine, polyethylene glycols, metallic lauryl sulfates and sodium chloride.

It will be understood that the percentages listed above for the filler and disintegrant component and lubricant are percentages each will comprise of a final pharmaceutical composition. The remainder of the final composition will be comprised of the active pharmacological agent(s) and a pharmaceutically acceptable surface covering, such as a coating or capsule, as described herein. In preferred aspects of this invention, the active pharmacological agent(s) will comprise from about 0.5% to about 20%, by weight, of the final composition, more preferably from about 1% to about 5%, and the coating or capsule will comprise up to about 8%, by weight, of the formulation.

Considering the filler and disintegrant component and lubricant component above, solely and without reference to an active pharmacological agent or coating, the carrier or excipient system would comprise:

a) from about 5.4% to about 89%, by weight, of a filler or disintegrant component, preferably from about 32.5% to about 87%; and b) from about 0.22% to about 10.9% of a lubricant component.

The carrier or excipient systems or compositions herein may also optionally utilize pharmaceutically acceptable wetting agents, glidants and antioxidants. Such systems or compositions comprise:

a) a filler and disintegrant component comprising from about 5% to about 82% by weight (wght) of the total formulation, preferably between about 30% and about 80% of the formulation, of which from about 4% to about 40% by weight of the total formulation comprises one or more pharmaceutically acceptable disintegrants;

b) optionally, a wetting agent comprising from about 0.2 to about 5% of the composition (wght), such as selected from the group of sodium lauryl sulfate, polyoxyethylene sorbitan fatty acid esters, polyoxyethylene alkyl ethers, sorbitan fatty acid esters, polyethylene glycols, polyoxyethylene castor oil derivatives, docusate sodium, quaternary ammonium compounds, sugar esters of fatty acids and glycerides of fatty acids;

c) a lubricant comprising from about 0.2% to about 10% of the composition (wght), such as selected from the group of magnesium stearate or other metallic stearates (e.g. calcium stearate or zinc stearate), fatty acid esters (e.g. sodium stearyl fumarate), fatty acids (e.g. stearic acid), fatty alcohols, glyceryl behenate, mineral oil, parrafins, hydrogenated vegetable oils, leucine, polyethylene glycols, metallic lauryl sulfates and sodium chloride; and d) optionally, a glidant comprising from about 0.1% to about 10% (wght) of the composition, the glidant selected from those known in the art, including from the group of silicon dioxide, talc, metallic stearates, calcium silicate, or metallic lauryl sulfates.

This invention also comprises solid oral formulations or compositions of a pharmaceutically effective dose of an active pharmacological compound, or a pharmaceutically acceptable salt thereof, and a carrier or excipient system of this invention, as described above. Among the more preferred active pharmacological agents for use with these carrier or excipients systems are non-steroidal estrogenic agents or tissues selective estrogenic agents. Examples of these compounds include, but are not limited to TSE-424, ERA-923, raloxifene, tamoxifen, droloxifene, arzoxifene or CP 336156, or a pharmaceutically acceptable salt of these compounds.

While the formulations described herein may be used in an uncoated or non-encapsulated solid form, preferably the final compositions are coated or encapsulated. The pharmacological compositions may be optionally coated with a film coating, preferably comprising from about 0.3% to about 8% by weight of the overall composition. Film coatings useful with the present formulations are known in the art and generally consist of a polymer (usually a cellulosic type of polymer), a colorant and a plasticizer. Additional ingredients such as wetting agents, sugars, flavors, oils and lubricants may be included in film coating formulations to impart certain characteristics to the film coat. The compositions and formulations herein may also be combined and processed as a solid, then placed in a capsule form, such as a gelatin capsule.

The filler component listed above may utilize the filler or binder components known in the art for solid oral formulations. Pharmaceutically acceptable fillers or binding agents selected from those known in the art including, but not limited to, lactose, microcrystalline cellulose, sucrose, mannitol, calcium phosphate, calcium carbonate, powdered cellulose, maltodextrin, sorbitol, starch, or xylitol.

In conjunction with or in place of the materials listed above for the filler component, the present formulations utilize disintegrant agents. These disintegrants may be selected from those known in the art, including pregelatinized starch and sodium starch glycolate. Other useful disintegrants include croscarmellose sodium, crospovidone, starch, alginic acid, sodium alginate, clays (e.g. veegum or xanthan gum), cellulose floc, ion exchange resins, or effervescent systems, such as those utilizing food acids (such as citric acid, tartaric acid, malic acid, fumaric acid, lactic acid, adipic acid, ascorbic acid, aspartic acid, erythorbic acid, glutamic acid, and succinic acid) and an alkaline carbonate component (such as sodium bicarbonate, calcium carbonate, magnesium carbonate, potassium carbonate, ammonium carbonate, etc.). The disintegrant(s) useful herein will comprise from about 4% to about 40% of the composition by weight, preferably from about 15% to about 35%, more preferably from about 20% to about 35%. Some components may have multiple functions in the formulations of this invention, acting e.g. as both a filler and a disintegrant, such a component may be referred to as a filler disintegrant and its function in a specific formulation may be singular even though its properties may allow multiple functionality.

The pharmaceutical formulations and carrier or excipient systems herein preferably also contain an antioxidant or a mixture of antioxidants, most preferably ascorbic acid. Other antioxidants which may be used include sodium ascorbate and ascorbyl palmitate, preferably in conjunction with an amount of ascorbic acid. A preferable range for the antioxidant(s) is from about 0.5% to about 15% by weight, most preferably from about 0.5% to about 5% by weight.

This invention further comprises pharmaceutical compositions comprising pharmaceutical carriers or excipients, as described above, and a pharmaceutically effective amount of a compound of the formulae I or II, below:

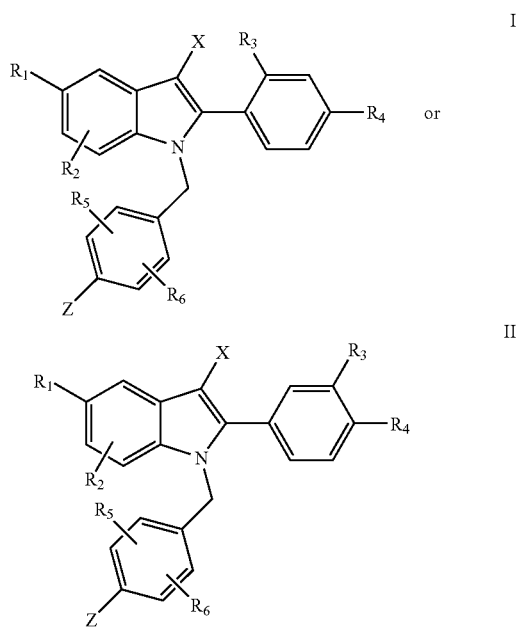

wherein Z is a moiety selected from the group of:

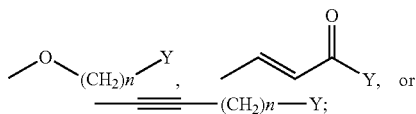

wherein:

$R_1$ is selected from H, OH or the $C_1$-$C_{12}$ esters (straight chain or branched) or $C_1$-$C_{12}$ (straight chain or branched or cyclic) alkyl ethers thereof, benzyloxy, or halogens; or $C_1$-$C_4$ halogenated ethers including trifluoromethyl ether and trichloromethyl ether;

$R_2$, $R_3$, $R_5$ and $R_6$ are independently selected from H, OH or the $C_1$-$C_{12}$ esters (straight chain or branched) or $C_1$-$C_{12}$ alkyl ethers (straight chain or branched or cyclic) thereof, halogens, or $C_1$-$C_4$ halogenated ethers including trifluoromethyl ether and trichloromethyl ether, cyano, $C_1$-$C_6$ alkyl (straight chain or branched), or trifluoromethyl, with the proviso that, when $R_1$ is H, $R_2$ is not OH;

$R_4$ is selected from H, OH or the $C_1$-$C_{12}$ esters (straight chain or branched) or $C_1$-$C_{12}$ alkyl ethers (straight chain or branched or cyclic) thereof, benzyloxy, halogens, or $C_1$-$C_4$ halogenated ethers including trifluoromethyl ether and trichloromethyl ether, cyano, $C_1$-$C_6$ alkyl (straight chain or branched), or trifluoromethyl;

X is selected from H, $C_1$-$C_6$ alkyl, cyano, nitro, trifluoromethyl, halogen;

n is 2 or 3;

Y is selected from:

a) the moiety:

wherein $R_7$ and $R_8$ are independently selected from the group of H, $C_1$-$C_6$ alkyl, or phenyl optionally substituted by CN, $C_1$-$C_6$ alkyl (straight chain or branched), $C_1$-$C_6$ alkoxy (straight chain or branched), halogen, —OH, —$CF_3$, or —$OCF_3$;

b) a five-membered saturated, unsaturated or partially unsaturated heterocycle containing up to two heteroatoms selected from the group consisting of —O—, —NH—, —N($C_1$-$C_4$ alkyl)-, —N=, and —S(O)$_m$—, wherein m is an integer of from 0-2, optionally substituted with 1-3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$) alkyl, —$CO_2$H—, —CN—, —CONH$R_1$—, —NH$_2$—, $C_1$-$C_4$ alkylamino, di($C_1$-$C_4$)alkylamino, —NHSO$_2$$R_1$—, —NHCO$R_1$—, —NO$_2$, and phenyl optionally substituted with 1-3 ($C_1$-$C_4$)alkyl;

c) a six-membered saturated, unsaturated or partially unsaturated heterocycle containing up to two heteroatoms selected from the group consisting of —O—, —NH—, —N($C_1$-$C_4$ alkyl)-, —N=, and —S(O)$_m$—, wherein m is an integer of from 0-2, optionally substituted with 1-3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$) alkyl, —$CO_2$H—, —CN—, —CONH$R_1$—, —NH$_2$—, $C_1$-$C_4$ alkylamino, di($C_1$-$C_4$)alkylamino, —NHSO$_2$$R_1$—, —NHCO$R_1$—, —NO$_2$, and phenyl optionally substituted with 1-3 ($C_1$-$C_4$)alkyl;

d) a seven-membered saturated, unsaturated or partially unsaturated heterocycle containing up to two heteroatoms selected from the group consisting of —O—, —NH—, —N($C_1$-$C_4$ alkyl)-, —N=, and —S(O)$_m$—, wherein m is an integer of from 0-2, optionally substituted with 1-3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$) alkyl, —$CO_2$H—, —CN—, —CONH$R_1$—, —NH$_2$—, $C_1$-$C_4$ alkylamino, di($C_1$-$C_4$)alkylamino, —NHSO$_2$$R_1$—, —NHCO$R_1$—, —NO$_2$, and phenyl optionally substituted with 1-3 ($C_1$-$C_4$)alkyl; or e) a bicyclic heterocycle containing from 6-12 carbon atoms either bridged or fused and containing up to two heteroatoms selected from the group consisting of —O—, —NH—, —N($C_1$-$C_4$ alkyl)-, and —S(O)$_m$—, wherein m is an integer of from 0-2, optionally substituted with 1-3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$) alkyl, —$CO_2$H—, —CN—, —CONH$R_1$—, —NH$_2$—, $C_1$-$C_4$ alkylamino, di($C_1$-$C_4$)alkylamino, —NHSO$_2$$R_1$—, —NHCO$R_1$—, —NO$_2$, and phenyl optionally substituted with 1-3 ($C_1$-$C_4$) alkyl;

and the pharmaceutically acceptable salts thereof.

This invention also comprises pharmaceutical compositions comprising pharmaceutical carriers or excipients, as described above, and a pharmaceutically effective amount of raloxifene, having the formula:

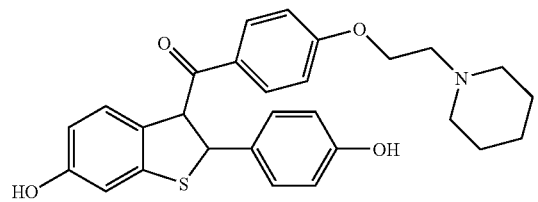

or its analogs or a pharmaceutically acceptable salt of raloxifene or its analogs, which are described in U.S. Pat. Nos. 4,133,814 (Jones et al.—issued Jan. 9, 1979) and 4,418,068 (Jones—issued Nov. 29, 1983), both of which are incorporated herein by reference. Among the most preferred of these formulations is a pharmaceutical composition comprising a carrier or excipient system, as described above, and a pharmaceutically effective amount of raloxifene or a pharmaceutically acceptable salt thereof. Preferably the salt is a hydrochloride salt of raloxifene.

Other formulations of this invention utilize as an active ingredient a pharmaceutically effective amount of Benzo[b]thiophene-6-ol,2-(4-methoxyphenyl)-3-[4-[2-(1-piperidinyl)ethoxy]phenoxy]-(9Cl), also known as Arzoxifene or LY 353381 (Registry No. 182133-25-1), or an analog or pharmaceutically acceptable salt form thereof, having the structure:

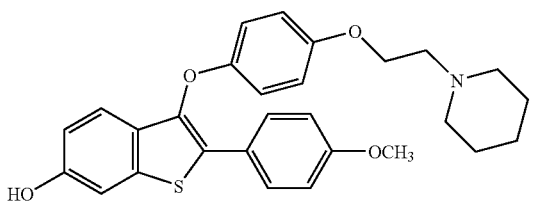

Arzoxifene and its analogs are disclosed in U.S. Pat. No. 5,510,358 (Palkowitz) and U.S. Pat. No. 5,919,800 (Palkowitz), which are incorporated herein by reference for their teaching of the synthesis of these compounds and representative salt forms thereof. Dosage forms of Arzoxifene and its analogs, or salt forms thereof, are preferably administered at a daily dosage level of from about 5 mg to about 600 mg. A preferred daily dosage may be from about 15 mg to about 80 mg in a single dose administration or in divided doses over a daily regimen.

Another embodiment of this invention comprises pharmaceutical formulations utilizing in conjunction with the carrier or excipient systems herein a pharmaceutically effective amount of the compound 2-Naphthalenol,5,6,7,8-tetrahydro-6-phenyl-5-[4-[2-(1-pyrrolidinyl)ethoxy]phenyl]-(5R,6S)-(2S,3S)-2,3-dihydroxybutanedioate(1:1) (salt) (9Cl), also known as CP 336156 (Registry No. 190791-29-8), having the structure:

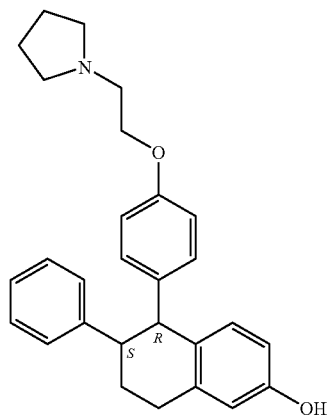

or analogs of CP 336156, or the pharmaceutically acceptable salts of CP 336156 or its analogs. These compounds are disclosed in WO 96/21656 (Cameron et al.), which is incorporated herein by reference to demonstrate the preparation and identity of these compounds. A pharmaceutically effective dose of these compounds may be delivered at a concentration of from about 0.1 mg to about 50 mg per day, preferably at a daily dosage of from about 0.5 mg to about 25 mg.

DETAILED DESCRIPTION OF THE INVENTION

The more preferred substituted indole compounds used in the formulations of this invention are those having the general structures I or II, above, wherein:

$R_1$ is selected from H, OH or the $C_1$-$C_{12}$ esters or alkyl ethers thereof, benzyloxy, or halogen;

$R_2$, $R_3$, $R_5$, and $R_6$ are independently selected from H, OH or the $C_1$-$C_{12}$ esters or alkyl ethers thereof, halogen, cyano, $C_1$-$C_6$ alkyl, or trihalomethyl, preferably trifluoromethyl, with the proviso that, when $R_1$ is H, $R_2$ is not OH;

$R_4$ is selected from H, OH or the $C_1$-$C_{12}$ esters or alkyl ethers thereof, benzyloxy, halogen, cyano, $C_1$-6 alkyl, or trihalomethyl;

X is selected from H, $C_1$-$C_6$ alkyl, cyano, nitro, trifluoromethyl, halogen;

Y is the moiety

$R_7$ and $R_8$ are selected independently from H, $C_1$-$C_6$ alkyl, or combined by —$(CH_2)_p$—, wherein p is an integer of from 2 to 6, so as to form a ring, the ring being optionally substituted by up to three substituents selected from the group of hydrogen, hydroxyl, halo, $C_1$-$C_4$ alkyl, trihalomethyl, $C_1$-$C_4$ alkoxy, trihalomethoxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —CONH($C_1$-$C_4$), —$NH_3$, $C_1$-$C_4$ alkylamino, $C_1$-$C_4$ dialkylamino, —$NHSO_2$($C_1$-$C_4$), —NHCO($C_1$-$C_4$), and —$NO_3$;

and the pharmaceutically acceptable salts thereof.

The rings formed by a concatenated $R_7$ and $R_8$, mentioned above, may include, but are not limited to, aziridine, azetidine, pyrrolidine, piperidine, hexamethyleneamine or heptamethyleneamine rings.

The most preferred indole compounds of the present invention are those having the structural formulas I or II, above, wherein $R_1$ is OH; $R_2$-$R_6$ are as defined above; X is selected from the group of $C_1$, $NO_2$, CN, $CF_3$, or $CH_3$; and Y is the moiety

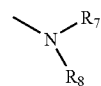

and $R_7$ and $R_8$ are concatenated together as —$(CH_2)_r$—, wherein r is an integer of from 4 to 6, to form a ring optionally substituted by up to three substituents selected from the group of hydrogen, hydroxyl, halo, $C_1$-$C_4$ alkyl, trihalomethyl, $C_1$-$C_4$ alkoxy, trihalomethoxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —CONH($C_1$-$C_4$)alkyl, —$NH_2$, $C_1$-$C_4$ alkylamino, di($C_1$-$C_4$)alkylamino, —$NHSO_2$($C_1$-$C_4$)alkyl, —NHCO($C_1$-$C_4$)alkyl, and —$NO_2$;

and the pharmaceutically acceptable salts thereof.

In another embodiment of this invention, when $R_7$ and $R_8$ are concatenated together as —$(CH_2)_p$—, wherein p is an integer of from 2 to 6, preferably 4 to 6, the ring so formed is optionally substituted with 1-3 substituents selected from a group containing $C_1$-$C_3$ alkyl, trifluoromethyl, halogen, hydrogen, phenyl, nitro, —CN.

The invention includes sulfate, sulfamates and sulfate esters of phenolic groups for the active compounds described above. Sulfates can be readily prepared by the reaction of the free phenolic compounds with sulfur trioxide complexed with an amine such as pyridine, trimethylamine, triethylamine, etc. Sulfamates can be prepared by treating the free phenolic compound with the desired amino or alkylamino or dialkylamino sulfamyl chloride in the presence of a suitable base such as pyridine. Sulfate esters can be prepared by reaction of the free phenol with the desired alkanesulfonyl chloride in the presence of a suitable base such as pyridine. Additionally, this invention includes compounds containing phosphates at the phenol as well as dialkyl phosphates. Phosphates can be prepared by reaction of the phenol with the appropriate chlorophosphate. The dialkylphosphates can be hydrolyzed to yield the free phosphates. Phosphinates are also claimed where the phenol is reacted with the desired dialkylphosphinic chloride to yield the desired dialkylphosphinate of the phenol.

The invention includes acceptable salt forms of these compounds formed from the addition reaction with either inorganic or organic acids. Inorganic acids such as hydrochloric acid, hydrobromic acid, hydroiodic acid, sulfuric acid, phosphoric acid, nitric acid useful as well as organic acids such as acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, benzenesulfonic acid are useful. It is known that compounds possessing a basic nitrogen can be complexed with many different acids (both protic and nonprotic) and usually it is preferred to administer a compound of this invention in the form of an acid addition salt. Additionally, this invention includes quaternary ammonium salts of the compounds herein. These can be prepared by reacting the nucleophilic amines of the side chain with a suitably reactive alkylating agent such as an alkyl halide or benzyl halide.

The present invention includes formulations utilizing a first subset or subgroup of compounds of the formulas IIII or IV, below:

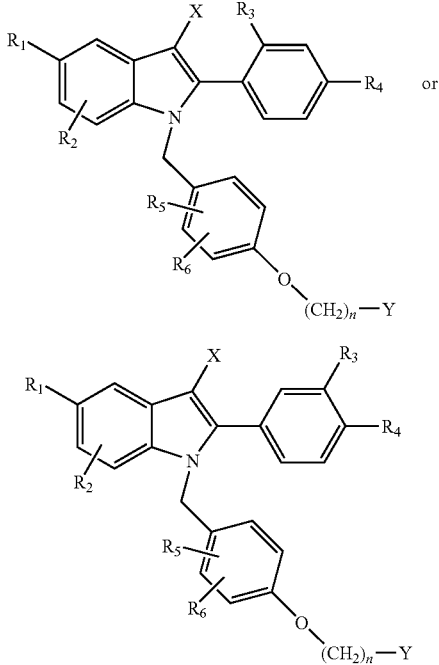

wherein the variable substituents including $R_1$, $R_2$, $R_3$, $R_4$, $R_5$, $R_6$, n, X, and Y are as defined above, or a pharmaceutically acceptable salt thereof.

The more preferred compounds of this first subset of compounds are those having the general structures III or IV, above, wherein:

$R_1$ is selected from H, OH or the $C_1$-$C_{12}$ esters or alkyl ethers thereof, benzyloxy, or halogen;

$R_2$, $R_3$, $R_5$, and $R_6$ are independently selected from H, OH or the $C_1$-$C_{12}$ esters or alkyl ethers thereof, halogen, cyano, $C_1$-$C_6$ alkyl, or trihalomethyl, preferably trifluoromethyl, with the proviso that, when $R_1$ is H, $R_2$ is not OH;

$R_4$ is selected from H, OH or the $C_1$-$C_{12}$ esters or alkyl ethers thereof, benzyloxy, halogen, cyano, $C_1$-$C_6$ alkyl, or trihalomethyl;

X is selected from H, $C_1$-$C_6$ alkyl, cyano, nitro, trifluoromethyl, halogen;

Y is the moiety

$R_7$ and $R_8$ are selected independently from H, $C_1$-$C_6$ alkyl, or combined by —$(CH_2)_p$—, wherein p is an integer of from 2 to 6, so as to form a ring, the ring being optionally substituted by up to three substituents selected from the group of hydrogen, hydroxyl, halo, $C_1$-$C_4$ alkyl, trihalomethyl, $C_1$-$C_4$ alkoxy, trihalomethoxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —$CONH(C_1$-$C_4)$, —$NH_3$, $C_1$-$C_4$ alkylamino, $C_1$-$C_4$ dialkylamino, —$NHSO_2(C_1$-$C_4)$, —$NHCO(C_1$-$C_4)$, and —$NO_3$;

and the pharmaceutically acceptable salts thereof.

The rings formed by a concatenated $R_7$ and $R_8$, mentioned above, may include, but are not limited to, aziridine, azetidine, pyrrolidine, piperidine, hexamethyleneamine or heptamethyleneamine rings.

The most preferred compounds of this first subset of compounds are those having the structural formulas I or II, above, wherein $R_1$ is OH; $R_2$-$R_6$ are as defined above; X is selected from the group of $C_1$, $NO_2$, CN, $CF_3$, or $CH_3$; and Y is the moiety

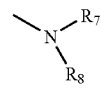

and $R_7$ and $R_8$ are concatenated together as —$(CH_2)_r$—, wherein r is an integer of from 4 to 6, to form a ring optionally substituted by up to three substituents selected from the group of hydrogen, hydroxyl, halo, $C_1$-$C_4$ alkyl, trihalomethyl, $C_1$-$C_4$ alkoxy, trihalomethoxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —$CONH(C_1$-$C_4)$alkyl, —$NH_2$, $C_1$-$C_4$ alkylamino, di($C_1$-$C_4$)alkylamino, —$NHSO_2(C_1$-$C_4)$alkyl, —$NHCO(C_1$-$C_4)$alkyl, and —$NO_2$;

and the pharmaceutically acceptable salts thereof.

In another embodiment of this first subset of compounds, when $R_7$ and $R_8$ are concatenated together as —$(CH_2)_p$—, wherein p is an integer of from 2 to 6, preferably 4 to 6, the ring so formed is optionally substituted with 1-3 substituents selected from a group containing $C_1$-$C_3$ alkyl, trifluoromethyl, halogen, hydrogen, phenyl, nitro, —CN.

Among the preferred compounds of this first subset are the following:

5-Benzyloxy-2-(4-ethoxy-phenyl)-3-methyl-1-[4-(2-piperidin-1-yl-ethoxy)-benzyl]-1H-1-indole;

5-Benzyloxy-2-phenyl-3-methyl-1-[4-(2-azepan-1-yl-ethoxy)-benzyl]-1H-indole;

5-Benzyloxy-2-(4-benzyloxy-phenyl)-3-methyl-1-[4-(2-azepan-1-yl-ethoxy)-benzyl]-1H-indole;

5-Benzyloxy-2-(4-benzyloxy-phenyl)-3-methyl-1-[4-(2-diisopropylamino-1-yl-ethoxy)benzyl]-1H-indole;

5-Benzyloxy-2-(4-benzyloxy-phenyl)-3-methyl-1-[4-(2-butyl-methylamino-1-ylethoxy)benzyl]-1H-indole;

5-Benzyloxy-2-(4-benzyloxy-phenyl)-3-methyl-1-{4-dimethylamino)-ethoxy]-benzyl}-1H-indole;

5-Benzyloxy-2-(4-benzyloxy-phenyl)-3-methyl-1-{4-[2-(2-methyl-piperidin-1-yl)-ethoxy]-benzyl}-1H-indole;

5-Benzyloxy-2-(4-benzyloxy-phenyl)-3-methyl-1-{4-[2-(3-methyl-piperidin-1-yl)-ethoxy]-benzyl}-1H-indole;

5-Benzyloxy-2-(4-benzyloxy-phenyl)-3-methyl-1-{4-[2-(4-methyl-piperidin-1-yl)-ethoxy]-benzyl}-1H-indole;

5-Benzyloxy-2-(4-benzyloxy-phenyl)-3-methyl-1{4-[2-((cis)-2,6-Dimethyl-piperidin-1-yl)ethoxy]-benzyl}-1H-indole;

5-Benzyloxy-2-(4-benzyloxy-phenyl)-3-methyl-{4-[2-(1,3,3-trimethyl-6-aza-bicyclo[3.2.1]oct-6-yl)-ethoxy]-benzyl}-1H-indole;

(1S,4R)-5-Benzyloxy-2-(4-benzyloxy-phenyl)-3-methyl{4-[2-(2-Aza-bicyclo[2.2.1]hept-2-yl)-ethoxy]-benzyl}-1H-indole;

5-Benzyloxy-2-(4-fluoro-phenyl)-3-methyl-1-[4-(2-azepan-1-yl-ethoxy)-benzyl]-1H-indole;

5-Benzyloxy-2-(4-fluoro-phenyl)-3-methyl-1-[4-(2-piperidin-1-yl-ethoxy)-benzyl]-1H-indole;

5-Benzyloxy-2-(4-chloro-phenyl)-3-methyl-1-[4-(2-piperidin-1-yl-ethoxy)-benzyl]-1H-indole;

5-Benzyloxy-2-[3,4-methylenedioxy-phenyl]-3-methyl-1-[4-(2-piperidin-1-yl-ethoxy)benzyl]-1H-indole;
5-Benzyloxy-2-[4-isopropoxy-phenyl]-3-methyl-1-[4-(2-piperidin-1-yl-ethoxy)-benzyl]-1H-indole;
5-Benzyloxy-2-[4-methyl-phenyl]-3-methyl-1-[4-(2-piperidin-1-yl-ethoxy)-benzyl]-1H-indole;
1-[4-(2-Azepan-1-yl-ethoxy)-benzyl]-5-benzyloxy-2-(3-benzyloxy-phenyl)-3-methyl-1H-indole;
5-Benzyloxy-2-(4-benzyloxy-3-fluoro-phenyl)-3-methyl-1-[4-(2-piperidin-1-yl-ethoxy)benzyl]-1H-indole;
5-Benzyloxy-2-(4-benzyloxy-3-fluoro-phenyl)-3-methyl-1-[4-(2-azepan-1-yl-ethoxy)benzyl]-1H-indole;
5-Benzyloxy-2-(3-methoxy-phenyl-1-[4-(2-piperidin-1-yl-ethoxy)-benzyl]-3-methyl-1H-indole;
5-Benzyloxy-3-methyl-1-[4-(2-piperidin-1-yl-ethoxy)-benzyl]-2-(4-trifluoromethoxyphenyl)-1H-indole;
(2-{4-[5-Benzyloxy-2-(4-benzyloxy-phenyl)-3-methyl-indol-1-ylmethyl]-phenoxy}-ethyl)cyclohexyl-amine;
5-Benzyloxy-2-(4-benzyloxy-phenyl)-3-methyl-1-{4-methylpiperazin-1-yl)-ethoxy]-benzyl}-1H-indole;
1-[4-(2-Azepan-1-yl-ethoxy)-benzyl]-5-benzyloxy-2-(3-methoxy-phenyl)-3-methyl-1H-indole;
4-{3-Methyl-1-[4-(2-piperidin-1-yl-ethoxy)-benzyl]-1H-indole};
4-{3-Methyl-1-[4-(2-piperidin-1-yl-ethoxy)-benzyl]-1H-indol-2-yl}-phenol;
3-Methyl-2-phenyl-1-[4-(2-piperidine-1-yl-ethoxy)-benzyl]-1H-indol-5-ol;
4-{5-Methoxy-3-methyl-1-{4-[2-(piperidin-1-yl)-ethoxy]-benzyl}-1H-indol-2-yl}-phenol;
2-(4-methoxy-phenyl)-3-methyl-1-{4-[2-(piperidin-1-yl)-ethoxy]-benzyl}-1H-indol-5-ol;
5-Methoxy-2-(4-methoxy-phenyl)-3-methyl-1-[4-(2-piperidin-1-yl-ethoxy)-benzyl]-1H-indole;
1-[4-(2-Azepan-1-yl-ethoxy)-benzyl]-5-methoxy-2-(4-methoxy-phenyl)-3-methyl-1H-indole;
2-(4-Ethoxy-phenyl)-3-methyl-1-[4-(2-piperidin-1-yl-ethoxy)-benzyl]-1H-indol-5-ol;
1-[4-(2-Azepan-1-yl-ethoxy)-benzyl]-2-(4-ethoxy-phenyl)-3-methyl-1H-indol-5-ol;
4-{5-Fluoro-3-methyl-1-[4-(2-piperidin-1-yl-ethoxy)-benzyl]-1H-indol-2-yl}-phenol;
1-[4-(2-Azepan-1-yl-ethoxy)-benzyl]-3-methyl-2-phenyl-1H-indol-5-ol;
2-(4-Hydroxy-phenyl)-3-methyl-1-[4-(2-pyrollidin-1-yl-ethoxy)-benzyl]-1H-indol-5-ol;
1-[4-(2-Azepan-1-yl-ethoxy)-benzyl]-2-(4-hydroxy-phenyl)-3-methyl-1H-indol-5-ol;
1-[4-(2-Azepan-1-yl-ethoxy)-benzyl]-2-(4-hydroxy-phenyl)-3-methyl-1H-indol-5-ol;
1-[4-(2-Azocan-1-yl-ethoxy)-benzyl]-2-(4-hydroxy-phenyl)-3-methyl-1H-indol-5-ol;
2-(4-Hydroxy-phenyl)-3-methyl-1-[4-(2-dimethyl-1-yl-ethoxy)-benzyl]-1H-indol-5-ol;
2-(4-Hydroxy-phenyl)-3-methyl-1-[4-(2-diethyl-1-yl-ethoxy)-benzyl]-1H-indol-5-ol;
1-[4-(2-Dipropylamino-ethoxy)-benzyl]-2-(4-hydroxy-phenyl)-3-methyl-1H-indol-5-ol;
1-[4-(2-Dibutylamino-ethoxy)-benzyl]-2-(4-hydroxy-phenyl)-3-methyl-1H-indol-5-ol;
1-[4-(2-Diisopropylamino-ethoxy)-benzyl]-2-(4-hydroxy-phenyl)-3-methyl-1H-indol-5-ol;
1-{4-[2-(Butyl-methyl-amino)-ethoxy]-benzyl}-2-(4-hydroxy-phenyl)-3-methyl-1H-indol-5-ol;
2-(4-Hydroxy-phenyl)-3-methyl-1-{4-[2-(2-methyl-piperidin-1-yl)-ethoxy]-benzyl}-1H-indol-5-ol;
2-(4-Hydroxy-phenyl)-3-methyl-1-{4-[2-(3-methyl-piperidin-1-yl)-ethoxy]-benzyl}-1H-indol-5-ol;
2-(4-Hydroxy-phenyl)-3-methyl-1-{4-[2-(4-methyl-piperidin-1-yl)-ethoxy]-benzyl}-1H-indol-5-ol;
1-{4-[2-(3,3-Dimethyl-piperidin-1-yl)-ethoxy]-benzyl}-2-(4-hydroxy-phenyl)-3-methyl-1H-indol-5-ol;
1-{4-[2-((cis)-2,6-Dimethyl-piperidin-1-yl)-ethoxy]-benzyl}-2-(4-hydroxy-phenyl)-3-methyl-1H-indol-5-ol;
2-(4-Hydroxy-phenyl)-1-{4-[2-(4-hydroxy-piperidin-1-yl)-ethoxy]-benzyl}-3-methyl-1H-indol-5-ol;
(1S,4R)-1-{4-[2-(2-Aza-bicyclo[2.2.1]hept-2-yl)-ethoxy]-benzyl}-2-(4-hydroxy-phenyl)-3-methyl-1H-indol-5-ol;
2-(4-Hydroxy-phenyl)-3-methyl-1-{4-[2-(1,3,3-trimethyl-6-aza-bicyclo[3.2.1]oct-6-yl)ethoxy]-benzyl}-1H-indol-5-ol;
2-(4-Fluoro-phenyl)-3-methyl-1-[4-(2-piperidine-1-yl-ethoxy)-benzyl]-1H-indol-5-ol;
1-[4-(2-Azepan-1-yl-ethoxy)-benzyl]-2-(4-fluoro-phenyl)-3-methyl-1H-indol-5-ol;
2-(3-Methoxy-4-hydroxy-phenyl)-3-methyl-1-[4-(2-piperidin-1-yl-ethoxy)-benzyl]-1H-indol-5-ol;
2-Benzo[1,3]dioxol-5-yl-3-methyl-1-[4-(2-piperidin-1-yl-ethoxy)-benzyl]-1H-indol-5-ol;
2-(4-Isopropoxy-phenyl)-3-methyl-1-[4-(2-piperidin-1-yl-ethoxy)-benzyl]-1H-indol-5-ol;
1-[4-(2-Azepan-1-yl-ethoxy)-benzyl]-2-(4-isopropoxy-phenyl)-3-methyl-1H-indol-5-ol;
2-(4-Cyclopenyloxy-phenyl)-3-methyl-1-[4-(2-piperidin-1-yl-ethoxy)-benzyl]-1H-indol-5-ol;
3-Methyl-1-[4-(2-piperidin-1-yl-ethoxy)-benzyl]-2-(4-trifluoromethyl-phenyl)-1H-indol-5-ol;
3-Methyl-1-[4-(2-piperidin-1-yl-ethoxy)-benzyl]-2-p-tolyl-1H-indol-5-ol;
2-(4-Chloro-phenyl)-3-methyl-1-[4-(2-piperidin-1-yl-ethoxy)-benzyl]-1H-indol-5-ol;
2-(2,4-Dimethoxy-phenyl)-3-methyl-1-[4-(2-piperidin-1-yl-ethoxy)-benzyl]-1H-indol-5-ol;
2-(3-Hydroxy-phenyl)-3-methyl-1-[4-(2-piperidin-1-yl-ethoxy)-benzyl]-1H-indol-5-ol;
1-[4-(2-Azepan-1-yl-ethoxy)-benzyl]-2-(3-hydroxy-phenyl)-3-methyl-1H-indole-5-ol;
2-(3-Fluoro-4-hydroxy-phenyl)-3-methyl-1-[4-(2-piperidin-1-yl-ethoxy)-benzyl]-1H-indol-5-ol;
2-(3-Fluoro-4-hydroxy-phenyl)-3-methyl-1-[4-(azepan-1-yl-ethoxy)-benzyl]-1H-indol-5-ol;
2-(3-Methoxy-phenyl)-3-methyl-1-[4-(2-piperidin-1-yl-ethoxy)-benzyl]-1H-indole-5-ol;
3-Methyl-1-[4-(2-piperidin-1-yl-ethoxy)-benzyl]-2-(4-trifluoromethoxy-phenyl)-1H-indole-5-ol;
3-Chloro-2-(4-hydroxy-phenyl)-1-[4-(2-pyrrolidin-1-yl-ethoxy)-benzyl]-1H-indol-5-ol;
3-Chloro-2-(4-hydroxy-phenyl)-1-[4-(2-piperidin-1-yl-ethoxy)-benzyl]-1H-indol-5-ol;
3-Chloro-2-(4-hydroxy-phenyl)-1-[4-(2-azepan-1-yl-ethoxy)-benzyl]-1H-indol-5-ol;
3-Chloro-2-(4-hydroxy-2-methyl-phenyl)-1-[4-(2-piperidin-1-yl-ethoxy)-benzyl]-1H-indol-1-5-ol;
2-(4-Hydroxy-phenyl)-3-ethyl-1-[4-(2-piperidin-1-yl-ethoxy)-benzyl]-1H-indol-5-ol;
5-Hydroxy-2-(4-Hydroxy-phenyl)-1-[4-(2-piperidin-1-yl-ethoxy)-benzyl]-1H-indole-3-carbonitrile;
1-[4-(2-Azepan-1-yl-ethoxy)-benzyl]-5-hydroxy-2-(4-hydroxy-phenyl)-1H-indole-3-cabonitrile;
5-Benzyloxy-2-(4-benzyloxy-phenyl)-3-chloro-1-[4-(2-piperidin-1-yl-ethoxy)-benzyl]-1H-indole;
5-Benzyloxy-2-(4-benzyloxy-phenyl)-3-chloro-1-[4-(2-azepan-1-yl-ethoxy)-benzyl]-1H-indole;
5-Benzyloxy-2-(2-methyl-4-benzyloxy-phenyl)-3-chloro-1-[4-(2-piperidin-1-yl-ethoxy)benzyl]-1H-indole;
5-Benzyloxy-2-(4-benzyloxy-phenyl)-3-ethyl-1-[4-(2-piperidin-1-yl-ethoxy)-benzyl]-1H-indole;
5-Benzyloxy-2-(4-benzyloxy-phenyl)-3-cyano-1-[4-(2-piperidin-1-yl-ethoxy)-benzyl]-1H-indole;

5-Benzyloxy-2-(4-benzyloxy-phenyl)-3-cyano-1-[4-(2-azepan-1-yl-ethoxy)-benzyl]-1H-indole;

Di-propionate of 1-[4-(2-Azepan-1-yl-ethoxy)-benzyl]-2-(4-hydroxy-phenyl)-3-methyl-1H-indol-5-ol;

Di-pivalate of 1-[4-(2-Azepan-1-yl-ethoxy)-benzyl]-2-(4-hydroxy-phenyl)-3-methyl-1H-indol-5-ol;

5-Benzyloxy-2-(4-benzyloxy-phenyl)-1-[4-(3-piperidin-1-yl-propoxy)-benzyl]-3-methyl-1H-indole;

2-(4-Hydroxy-phenyl)-3-methyl-1-{4-[3-(piperidin-1-yl)-propoxy]-benzyl}-1H-indol-5-ol;

2-(4-Hydroxy-phenyl)-1-[3-methoxy-4-(2-piperidin-1-yl-ethoxy)-benzyl]-3-methyl-1H-indol-5-ol;

2-(4-Hydroxy-phenyl)-1-[3-methoxy-4-(2-azepan-1-yl-ethoxy)-benzyl]-3-methyl-1H-indol-5-ol;

5-Benzyloxy-2-(4-benzyloxy-phenyl)-3-methyl-1-[3-Methoxy-4-(2-piperidin-1-yl-ethoxy)benzyl]-1H-indole;

5-Benzyloxy-2-(4-benzyloxy-phenyl)-3-methyl-1-[2-Methoxy-4-(2-azepan-1-yl-ethoxy)benzyl]-1H-indole;

2-(4-Hydroxy-phenyl)-3-methyl-1-[4-(2-piperidin-1-yl-ethoxy)-benzyl]-1H-indol-5-ol; or the pharmaceutically acceptable salts thereof.

The compounds of this first subset or subgroup of compounds can be produced by the methods described in EP 0 802 183 A1, published Oct. 22, 1997, and U.S. Pat. No. 5,780,497, the subject matter of which is incorporated herein by reference, or by other methods known in the art. Aryloxy-alkyl-dialkylamines or aryloxy-alkyl-cyclic amines useful as intermediates in the production of the compounds above can be produced and used as disclosed in WO 99/19293, published Apr. 22, 1999, the subject matter of which is also incorporated herein by reference.

A second subset or subgroup of compounds useful with the formulations of this invention includes those of formulas (V) or (VI), below:

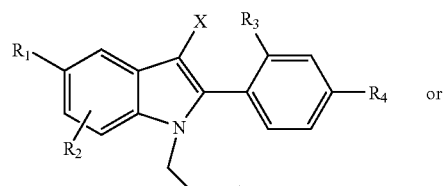
(V)

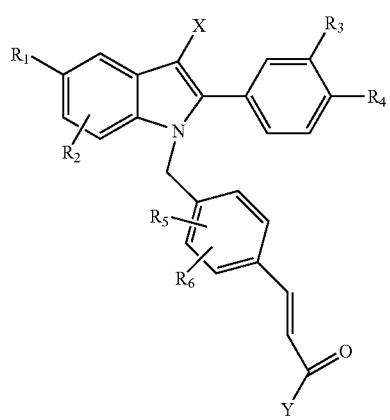
(VI)

wherein the variable substituents including $R_1$, $R_2$, $R_3$, $R_4$, $R_5$, $R_6$, n, X, and Y are as defined above, or a pharmaceutically acceptable salt thereof.

Among the preferred compounds of this second subset or subgroup are the following:

(E)-N,N-Diethyl-3-{4-[5-hydroxy-2-(4-hydroxy-phenyl)-3-methyl-indol-1-ylmethyl]-phenyl}-acrylamide;

1 (E)-N-tert-butyl-3-{4-[5-hydroxy-2-(4-hydroxy-phenyl)-3-methyl-indol-1-ylmethyl]-phenyl}-acrylamide;

(E)-Pyrollidino-3-{4-[5-hydroxy-2-(4-hydroxy-phenyl)-3-methyl-indol-1-ylmethyl]-phenyl}-acrylamide;

(E)-N,N-Dimethyl-3-{4-[5-hydroxy-2-(4-hydroxy-phenyl)-3-methyl-indol-1-ylmethyl]-phenyl}-acrylamide;

(E)-N,N-Dibutyl-3-{4-[5-hydroxy-2-(4-hydroxy-phenyl)-3-methyl-indol-1-ylmethyl]-phenyl}-acrylamide;

(E)-N-Butyl, N'-methyl-3-{4-[5-hydroxy-2-(4-hydroxy-phenyl)-3-methyl-indol-1-ylmethyl]-phenyl}-acrylamide;

(E)-Morpholinino-3-{4-[5-hydroxy-2-(4-hydroxy-phenyl)-3-methyl-indol-1-ylmethyl]-phenyl}-acrylamide;

(E)-3-{4-[5-hydroxy-2-(4-hydroxy-phenyl)-3-methyl-indol-1-ylmethyl]-phenyl}-acrylamide;

(E)-N,Methyl-3-{4-[5-hydroxy-2-(4-hydroxy-phenyl)-3-methyl-indol-1-ylmethyl]-phenyl}-acrylamide;

(E)-N,N-Dibutyl-3-{4-[5-hydroxy-2-(4-fluoro-phenyl)-3-methyl-indol-1-ylmethyl]-phenyl}-acrylamide;

(E)-N-Butyl, N'-Methyl-3-{4-[5-hydroxy-2-(4-fluoro-phenyl)-3-methyl-indol-1-ylmethyl]-phenyl}-acrylamide;

as well as the pharmaceutically acceptable salts and esters thereof.

The compounds of this second subset or subgroup of compounds can be produced by the methods described in EP 0 802 184 A1, published Oct. 22, 1997, which is incorporated herein by reference, or by other methods known in the art.

A third subset of compounds useful with the present invention include those of the formulae VII and VIII:

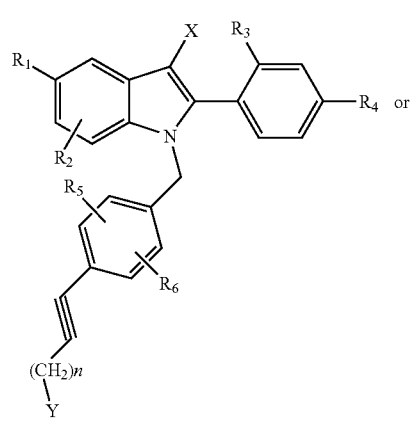
(VII)

-continued

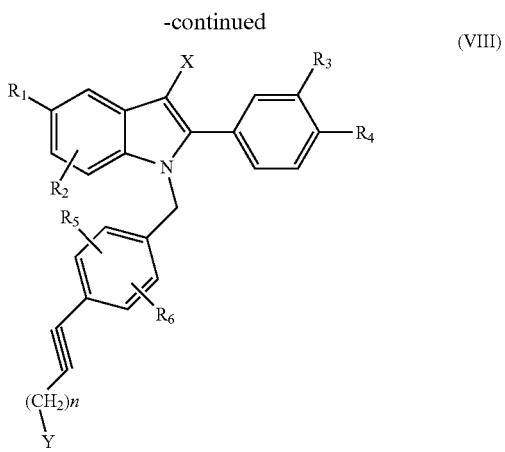

(VIII)

wherein n is 1, 2 or 3 and the variable substituents including $R_1$, $R_2$, $R_3$, $R_4$, $R_5$, $R_6$, n, X, and Y are as defined above, or a pharmaceutically acceptable salt thereof.

Among the preferred compounds of this third subset are:
2-(4-Hydroxy-phenyl)-3-methyl-1-[4-(3-N,N-dimethyl-1-yl-prop-1-ynyl)-benzyl]-1H-indol-5-ol;
2-(4-Hydroxy-phenyl)-3-methyl-1-[4-(3-piperidin-1-yl-prop-1-ynyl)-benzyl]-1H-indol-5-ol; and
2-(4-Hydroxy-phenyl)-3-methyl-1-[4-(3-pyrrolidin-1-yl-prop-1-ynyl)-benzyl]-1H-indol-5-ol;
or pharmaceutically acceptable salts or esters thereof.

The compounds of this third subset or subgroup of compounds can be produced by the methods described in U.S. Pat. No. 5,880,137 (Miller et al.), which is incorporated herein by reference, or by other methods known in the art.

Within each of the first, second and third subsets of compounds of this invention are further subdivisions of more preferred compounds having the general structures I through VIII, above, wherein:

$R_1$ is selected from H, OH or the $C_1$-$C_{12}$ esters or alkyl ethers thereof, halogen;

$R_2$, $R_3$, $R_4$, $R_5$, and $R_6$ are independently selected from H, OH or the $C_1$-$C_{12}$ esters or alkyl ethers thereof, halogen, cyano, $C_1$-$C_6$ alkyl, or trihalomethyl, preferably trifluoromethyl, with the proviso that, when $R_1$ is H, $R_2$ is not OH;

X is selected from H, $C_1$-$C_6$ alkyl, cyano, nitro, trifluoromethyl, halogen;

Y is the moiety

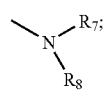

$R_7$ and $R_8$ are selected independently from H, $C_1$-$C_6$ alkyl, or combined by —$(CH_2)_p$—, wherein p is an integer of from 2 to 6, so as to form a ring, the ring being optionally substituted by up to three substituents selected from the group of hydrogen, hydroxyl, halo, $C_1$-$C_4$ alkyl, trihalomethyl, $C_1$-$C_4$ alkoxy, trihalomethoxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —$CONH(C_1$-$C_4)$, —$NH_3$, $C_1$-$C_4$ alkylamino, $C_1$-$C_4$ dialkylamino, —$NHSO_2$ ($C_1$-$C_4$), —$NHCO(C_1$-$C_4)$, and —$NO_3$;

and the pharmaceutically acceptable salts thereof.

The rings formed by a concatenated $R_7$ and $R_8$, mentioned above, may include, but are not limited to, aziridine, azetidine, pyrrolidine, piperidine, hexamethyleneamine or heptamethyleneamine rings.

The most preferred compounds of the present invention are those having the structural formulas I through VIII, above, wherein $R_1$ is OH; $R_2$-$R_6$ are as defined above; X is selected from the group of $C_1$, $NO_2$, CN, $CF_3$, or $CH_3$; and Y is the moiety

and $R_7$ and $R_8$ are concatenated together as —$(CH_2)_r$, wherein r is an integer of from 4 to 6, to form a ring optionally substituted by up to three substituents selected from the group of hydrogen, hydroxyl, halo, $C_1$-$C_4$ alkyl, trihalomethyl, $C_1$-$C_4$ alkoxy, trihalomethoxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —$CONH(C_1$-$C_4)$alkyl, —$NH_2$, $C_1$-$C_4$ alkylamino, di($C_1$-$C_4$)alkylamino, —$NHSO_2(C_1$-$C_4)$alkyl, —$NHCO(C_1$-$C_4)$alkyl, and —$NO_2$;

and the pharmaceutically acceptable salts thereof.

In another embodiment of this invention, when $R_7$ and $R_8$ are concatenated together as —$(CH_2)_p$—, wherein p is an integer of from 2 to 6, preferably 4 to 6, the ring so formed is optionally substituted with 1-3 substituents selected from a group containing $C_1$-$C_3$ alkyl, trifluoromethyl, halogen, hydrogen, phenyl, nitro, —CN.

Aryloxy-alkyl-dialkylamine intermediates useful in preparing the substituted indole compounds of this invention can be synthesized as described in WO 99/19293 (Raveendranath et al.), which is incorporated herein by reference.

It is understood that the dosage and regimen of these compounds and formulations will vary according to the malady and the individual being treated and will be subject to the judgement of the medical practitioner involved. It is preferred that the administration of one or more of the compounds herein begin at a low dose and be increased until the desired effects are achieved.

Pharmaceutically effective administration of these compounds may be given at an effective dose of from about 0.1 mg/day to about 1,000 mg/day. Preferably, administration will be from about 10 mg/day to about 600 mg/day in a single dose or in two or more divided doses. More preferably, administration will be from about 1 mg/day to about 200 mg/day in a single dose or in two or more divided doses. It will also be understood that these methods and regimens may be completed either remedially or prophylactically in the treatment, prohibition, inhibition or alleviation of the causes and symptoms of the maladies in question.

When the active ingredient in the formulations and methods of this invention is 1-[4-(2-Azepan-1yl-ethoxy)-benzyl]-2-(4-hydroxy-phenyl)-3-methyl-1H-indol-5-ol, also known as TSE-424, or a pharmaceutically acceptable salt thereof, the preferred daily dosage for oral delivery is from about 0.1 to about 50 mg, preferably from about 2.5 to about 40 mg per day.

When the active ingredient in the formulations and methods of this invention is 2-(4-Hydroxy-phenyl)-3-methyl-1-(4-(2-piperidin-1-yl-ethoxy)-benzyl]-1H-indol-5-ol, also known as ERA-923, or a pharmaceutically acceptable salt form thereof, the preferred daily dosage for oral delivery is from about 0.1 to about 200 mg, preferably from about 2.5 to about 100 mg per day.

Oral formulations containing the active compounds of this invention may comprise any conventionally used oral forms, including tablets, capsules, buccal forms, troches, lozenges and oral suspensions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

Among the most preferred active pharmacological agents of this invention are 1-[4-(2-Azepan-1yl-ethoxy)-benzyl]-2-(4-hydroxy-phenyl)-3-methyl-1H-indol-5-ol, also known as TSE-424, and 2-(4-Hydroxy-phenyl)-3-methyl-1-(4-(2-piperidin-1-yl-ethoxy)-benzyl]-1H-indol-5-ol, also known as ERA-923, or a pharmaceutically acceptable salt of TSE-424 or ERA-923.

Among the formulations of this invention are pharmaceutical formulations containing a pharmaceutically effective amount of an active pharmacological agent and a carrier or excipient system comprising:

a) a filler and disintegrant component comprising between about 50% and about 87% of the formulation, with from about 4% to about 40% of the formulation comprising one or more disintegrant agents;

b) a wetting agent comprising between about 0.5% and about 2.7% of the formulation;

c) a lubricant comprising between about 0.2% and about 5.5% of the formulation; and d) a glidant comprising between about 0.1% and about 5.5% of the formulation.

The percentages listed in the formulations above indicate percentages by weight of the total weight of the components listed from a) to d). The formulations above also preferably contain an optional antioxidant component, preferably ascorbic acid, at a concentration of from about 0.5% to about 5.5% by weight of the formulation. The formulations are also preferably contained within a pharmaceutically acceptable capsule, such as a gel capsule, or coated with a film coating comprising from about 0.3% to about 8% by weight of the formulation.

This invention also comprises a pharmaceutical carrier or excipient systems useful in pharmaceutical compositions utilizing as an active ingredient one or more of the compounds described herein, or a pharmaceutically acceptable salt thereof, as described herein. These pharmaceutical carrier or excipient systems comprise, by weight:

a) a filler and disintegrant component comprising between about 54% and about 80% of the formulation, with the disintegrant agent(s) therein comprising from about 4% to about 40% by weight of the overall formulation;

b) a wetting agent comprising between about 0.55% and about 2.5% of the formulation;

c) a lubricant comprising between about 0.2% and about 5.5% of the formulation; and d) a glidant comprising between about 0.1% and about 5.0% of the formulation.

The more preferred carrier or excipient systems above also optionally and preferably contain an antioxidant component, preferably ascorbic acid, at a concentration of from about 0.5% to about 5.0% by weight.

Among the carrier or excipient systems of this invention are those comprising:

a) a filler and disintegrant component, as described above, comprising between about 50% and about 87% of the formulation, the disintegrant(s) therein comprising from about 25% to about 35% of the formulation, by weight;

b) a wetting agent comprising between about 0.55% and about 2.7% of the formulation;

c) a lubricant comprising between about 0.2% and about 5.5% of the formulation;

d) a glidant comprising between about 0.1% and about 5.5% of the formulation; and e) an antioxidant component, preferably ascorbic acid, at a concentration of from about 0.5% to about 5.5% by weight.

It will be understood that the carrier or excipient systems herein may also be used as described to produce comparable pharmaceutical compositions or formulations containing other non-steroidal estrogenic agents, such as raloxifene, tamoxifen, droloxifene, arzoxifene or CP 336156 and/or an analog of these compounds, or a pharmaceutically acceptable salt of the compounds or their analogs, as an active pharmacological agent.

The raloxifene-containing compositions of this invention may be administered with raloxifene being given at a daily dose of from about 0.1 mg to about 1,000 mg, as a single daily unit dose or administered in two or more doses over the course of the day. More preferably, the daily unit doses of these compositions will comprise a dose of raloxifene or its salt form at from about 50 mg to about 400 mg, more preferably from about 50 mg to about 200 mg.

A specifically preferred raloxifene formulation herein may comprise a carrier or excipient system of this invention and raloxifene, or a pharmaceutically acceptable salt thereof, at a pharmaceutically effective dose of from about 55 mg to about 150 mg or from about 60 mg to about 150 mg.

EXAMPLE 1

TSE-424 Acetate—Rapid Dissolution Formulations

| Ingredient | without Ascorbic Acid | with Ascorbic Acid |
|---|---|---|
| TSE-424 acetate, micronized* | 10.00 | 10.00 |
| Lactose NF fast flow | 33.10 | 31.60 |
| Microcrystalline Cellulose, NF (Avicel PH101) | 25.00 | 25.00 |
| Starch 1500 | 20.00 | 20.00 |
| Sodium Lauryl Sulfate NF | 1.50 | 1.50 |
| Sodium Starch Glycolate | 10.00 | 10.00 |
| Ascorbic Acid USP | — | 1.5 |
| Syloid 244 FP | 0.15 | 0.15 |
| Magnesium Stearate | 0.25 | 0.25 |

*Amount in formula is adjusted for actual potency of TSE-424 as free base. Corresponding adjustment made with Lactose.

The formulations given above in Table 1 were prepared by incorporating a portion of the excipients in the granulation and a portion is also added in the final blending steps as dry powders. A dissolution profile generated for the formulations demonstrated almost 90% release of the drug in 30 minutes. Thus, the unique combination of disintegrants and soluble diluents plus the incorporation of both granulated and powdered solids into the composition ensures the fastest release of drug.

EXAMPLE 2

TSE-424 Formulations

| | % w/w | | | Ranges | |
|---|---|---|---|---|---|
| | 1% | 5% | | | |
| Ingredient | granulation | granulation | Function | Preferred | Possible |
| TSE-424 acetate, micronized[a] | 1.00 | 5.00 | Active | 5-18 | 0.1-25 |
| Lactose NF | 20.00 | 20.00 | Filler | 47-77 | 20-80 |
| Microcrystalline Cellulose, NF | 45.60 | 41.60 | Filler/Binder/Disintegrant | | |
| Pregelatinized Starch NF | 20.00 | 20.00 | Disintegrant | 25-35 | 4-40 |
| Sodium Starch Glycolate NF | 10.00 | 10.00 | Disintegrant | | |
| Sodium Lauryl Sulfate NF | 1.50 | 1.50 | Wetting agent | 1-2 | 0.2-5 |
| l-Ascorbic Acid USP | 1.50 | 1.50 | Antioxidant | 1-3 | 0.5-15 |
| Silicon Dioxide NF (Syloid 244 FP) | 0.15 | 0.15 | Glidant | 0.1-0.5 | 0.1-10 |
| Magnesium Stearate NF | 0.25 | 0.25 | Lubricant | 0.2-0.5 | 0.2-10 |
| Pur. Water USP[b] | qs | qs | Granulating solvent | — | — |

| Dose of TSE-424 | granulation used | tablet weight, mg | mg of film coat applied/tablet[c] |
|---|---|---|---|
| 1 mg | 1% | 100 | 6.0 |
| 2.5 mg | 1% | 250 | 10.0 |
| 5 mg | 5% | 100 | 6.0 |
| 10 mg | 5% | 200 | 8.0 |
| 20 mg | 5% | 400 | 13.0 |

[a]Amount in formula is adjusted for actual potency of TSE-424 as free base. Corresponding adjustment made with MCC.
[b]Used in process but does not appear in the final product.
[c]The film coating suspension is made using White Opadry II (YS-30-18105) and Purified Water Wet granulation of the formulations as described in Table 1 may be carried out by mixing the drug and ascorbic acid with a portion of the lactose, microcrystalline cellulose, pregelatinized starch and sodium starch glycolate. The sodium lauryl sulfate is dissolved in the water and used to granulate the mixture of powders in a high shear mixer. The granulation is dried in a fluid bed dryer to a moisture of 2-3%. The particle size of the dried granulation is controlled by passing through a mill equipped with knife-edged blades and using a 20- or 30-mesh screen. The silicon dioxide and remaining lactose, microcrystalline cellulose, pregelatinized starch, and sodium starch glycolate are mixed with the milled granulation in a tumble-type mixer. The final blend is prepared by adding magnesium stearate to the tumble-type mixer and mixing. Compression is carried out on a rotary tablet press using appropriate size tooling. Coating is performed in conventional coating pans and applying the coating suspension to achieve a suitable film coat.

EXAMPLE 3

Modified TSE-424 Formulation

| Ingredient | % w/w 5% granulation |
|---|---|
| TSE-424 acetate, micronized[a] | 5.00 |
| Lactose NF | 41.00 |
| Microcrystalline Cellulose, NF | 35.00 |
| Pregelatinized Starch NF | 10.00 |
| Sodium Lauryl Sulfate NF | 1.50 |
| l-Ascorbic Acid USP | 1.50 |
| Sodium Starch Glycolate NF | 5.50 |
| Magnesium Stearate NF | 0.50 |
| Pur. Water USP[b] | qs |

[a]Amount in formula is adjusted for actual potency of TSE-424 as free base. Corresponding adjustment made with Lactose.
[b]Used in process but does not appear in the final product.

EXAMPLE 4

ERA-923 Formulations

| Ingredient | 10.86% granulation % w/w | 11.19% granulation % w/w | 17.5% granulation % w/w | 17.9% granulation % w/w |
|---|---|---|---|---|
| ERA-923, micronized[a] | 10.867 | 11.193 | 17.489 | 17.909 |
| Lactose NF | 29.000 | 29.000 | 17.380 | 18.000 |
| Microcrystalline Cellulose, NF | 40.633 | 42.807 | 38.000 | 39.090 |
| Pregelatinized Starch NF | 10.000 | 10.000 | 14.630 | 15.000 |
| Sodium Lauryl Sulfate NF | 2.500 | — | 2.500 | — |
| l-Ascorbic Acid USP | 1.500 | 1.500 | 1.500 | 1.500 |
| Sodium Starch Glycolate NF | 5.000 | 5.000 | 8.000 | 8.000 |
| Magnesium Stearate NF | 0.500 | 0.500 | 0.500 | 0.500 |
| Pur. Water USP[b] | qs | qs | qs | qs |

[a]As the Hydrochloride Monohydrate. Quantity is adjusted based on the actual potency (theory = 89.34%).
[b]Used in process but does not appear in the final product.

ERA-923 tablets are compressed to a tablet weight of up to 640 mg to achieve the target dose (up to 100 mg). Tablets may then be film coated.

EXAMPLE 5

Stability with Ascorbic Acid as Antioxidant

Formulations of this invention containing 1% active ingredient (TSE-424) were prepared for stability comparison of formulations with and without ascorbic acid present over periods of 1, 3 and 6 months at either 25° C. and 60% relative humidity (RH) or 40° C. and 75% relative humidity. The stability data for these formulations are provided below, demonstrating that the ascorbic acid component provided protection of the estrogenic agent (TSE-424) versus oxidation in solid dosage formulations.

| Storage Condition | 1% capsule without Ascorbic Acid Strength (% label claim) | 1% capsule without Ascorbic Acid Total degradation products | 1% tablet with Ascorbic Acid Strength (% label claim) | 1% tablet with Ascorbic Acid Total degradation products |
|---|---|---|---|---|
| Initial | 101.4 | 0.20 | 100.5 | 0.46 |
| 25° C./60% RH 1 Month | 101.7 | 0.85 | 97.2 | 0.99 |
| 25° C./60% RH 3 Months | 99.3 | 1.63 | 98.6 | 0.55 |
| 25° C./60% RH 6 Months | 98.2 | 2.22 | 99.6 | 0.77 |
| 25° C./60% RH 9 Months | 95.7 | 2.77 | 99.1 | 0.88 |
| 40° C./75% RH 1 Month | 101.0 | 0.87 | 97.8 | 0.96 |
| 40° C./75% RH 3 Months | 97.8 | 1.86 | 98.5 | 0.55 |
| 40° C./75% RH 6 Months | 99.8 | 2.49 | 98.8 | 0.75 |

Note:
samples are stored in bottles.

EXAMPLE 6

TSE-424 at 5% Granulation

A preferred carrier or excipient system for formulating a granulation of from about 2 to about 8% by weight of one of the active pharmacological agents of this invention, preferably about 5%, may be produced utilizing the carrier or excipient components on a weight percentage; lactose from about 32% to about 38%, microcrystalline cellulose from about 32% to about 38%, pregelatinized starch from about 12% to about 16%, ascorbic acid from about 1% to about 2%, sodium lauryl sulfate from about 1% to about 2%, sodium starch glycolate from about 4% to about 8%, silicon dioxide from about 0.1% to about 0.2% and magnesium stearate from about 0.3% to about 0.7%.

A formulation of this invention utilizing TSE-424 as the active ingredient at a 5% granulation was prepared utilizing the components listed below in a granulation part of components and a dry part.

| Item No. | Ingredients | Mg/Unit |
|---|---|---|
| | Granulation Part: | |
| 1 | TSE-424 acetate | 5.00 |
| 2 | Lactose NF | 26.60 |
| 3 | Microcrystalline Cellulose NF | 25.00 |

-continued

| Item No. | Ingredients | Mg/Unit |
|---|---|---|
| 4 | Pregelatinized Starch NF | 10.00 |
| 5 | Ascorbic Acid USP | 1.50 |
| 6 | Sodium Lauryl Sulfate NF | 1.50 |
| 7 | Sodium Starch Glycolate NF | 4.00 |
| 8 | Water, Purified USP | Q.S. |
|  |  | 73.60 |
|  | Dry Part: |  |
| 9 | Lactose NF (fast flo) | 9.75 |
| 10 | Microcrystalline Cellulose NF | 10.00 |
| 11 | Pregelatinized Starch NF | 4.00 |
| 12 | Sodium Starch Glycolate NF | 2.00 |
| 13 | Silicon Dioxide NF | 0.15 |
| 14 | Magnesium Stearate NF | 0.50 |
|  |  | 100.00 |

A film coat of White Opadry I (YS-1-18027-A) was applied to the tablets, which were compressed as follows:

| Dose of TSE-424 | tablet weight, mg | mg of film coat applied/tablet |
|---|---|---|
| 5 mg | 100 | 6.0 |
| 10 mg | 200 | 8.0 |
| 20 mg | 400 | 13.0 |

Raloxifene HCl Formulations

Utilizing the methods described above, formulations of this invention may be produced with a carrier or excipient system utilizing the components of Examples 7 through 9. The percentages listed below represent the weight percentage of each component to the overall weight of the excipient or carrier system. Each formulation may then be formed into tablets, spheroids or other solid dosage forms of the desired size and coated as described herein. These formulations include those comprising raloxifene HCl as an active pharmacological agent at the unit doses described above, specifically including unit doses of 50 mg, 60 mg, 75 mg, 100 mg and 150 mg.

|  | Component | % Composition (w/w) |
|---|---|---|
| Example 7 | lactose | 35% |
|  | microcrystalline cellulose | 34% |
|  | starch | 20% |
|  | sodium lauryl sulfate | 2% |
|  | magnesium stearate | 1% |
|  | talc | 6.5% |
|  | ascorbic acid | 1.5% |
| Example 8 | microcrystalline cellulose | 50% |
|  | sucrose | 20% |
|  | sodium starch glycolate | 9.8% |
|  | powdered cellulose | 5% |
|  | sorbitan monolaurate | 5% |
|  | calcium stearate | 8% |

-continued

|  | Component | % Composition (w/w) |
|---|---|---|
|  | silicon dioxide | 0.2% |
|  | sodium ascorbate | 2% |
| Example 9 | mannitol | 45.5% |
|  | microcrystalline cellulose | 25% |
|  | polyoxyol 20 cetostaryl ether | 5% |
|  | crospovidone | 4% |
|  | stearic acid | 10% |
|  | calcium silicate | 0.5% |
|  | ascorbic acid | 10% |

Maintaining a low moisture content in the dried granulation compositions and the final products of this invention also enhances the stability of the resulting compositions.

What is claimed is:

1. A pharmaceutical composition comprising, by weight:
  a) from about 2% to about 8% 1-[4-(2-Azepan-1yl-ethoxy)-benzyl]-2-(4-hydroxyphenyl)-3-methyl-1H-indol-5-ol or 2-(4-Hydroxy-phenyl)-3-methyl-1-(4-(2-piperidin-1-yl-ethoxy)benzyl]-1H-indol-5-ol, or a pharmaceutically acceptable salt thereof;
  b) lactose from about 32% to about 38%;
  c) microcrystalline cellulose from about 32% to about 38%;
  d) pregelatinized starch from about 12% to about 16%;
  e) ascorbic acid from about 1% to about 2%;
  f) sodium lauryl sulfate from about 1% to about 2%;
  g) sodium starch glycolate from about 4% to about 8%;
  h) silicon dioxide from about 0.1% to about 0.2%; and
  i) magnesium stearate from about 0.3% to about 0.7%.

2. A pharmaceutical composition comprising, by weight:
  a) from 0.1% to 25% 1-[4-(2-Azepan-1yl-ethoxy)-benzyl]-2-(4-hydroxy-phenyl)-3-methyl-1H-indol-5-ol or 2-(4-Hydroxy-phenyl)-3-methyl-1-(4-(2-piperidin-1-yl-ethoxy)-benzyl]-1H-indol-5-ol, or a pharmaceutically acceptable salt thereof;
  b) from about 20% to about 80% lactose;
  c) from about 4% to about 40% pregelatinized starch;
  d) from about 0.2% to about 5% sodium lauryl sulfate;
  e) from about 0.5% to about 15% ascorbic acid;
  f) from about 0.1% to about 10% silicon dioxide; and
  g) from about 0.2% to about 10% magnesium stearate.

3. A pharmaceutical composition of claim 2 comprising, by weight:
  a) from about 5% to about 18% 1-[4-(2-Azepan-1yl-ethoxy)-benzyl]-2-(4-hydroxyphenyl)-3-methyl-1H-indol-5-ol or 2-(4-Hydroxy-phenyl)-3-methyl-1-(4-(2-piperidin-1-yl-ethoxy)benzyl]-1H-indol-5-o l, or a pharmaceutically acceptable salt thereof;
  b) from about 47% to about 77% lactose;
  c) from about 25% to about 35% pregelatinized starch;
  d) from about 1% to about 2% sodium lauryl sulfate;
  e) from about 1% to about 3% ascorbic acid;
  f) from about 0.1% to about 0.5% silicon dioxide; and
  g) from about 0.2% to about 0.5% magnesium stearate.

* * * * *